US012687538B2

(12) United States Patent (10) Patent No.: US 12,687,538 B2
Mizutani (45) Date of Patent: Jul. 21, 2026

(54) PLANT STATE DETECTION SYSTEM AND ODOR DETECTOR

(71) Applicant: SINTOKOGIO, LTD., Nagoya (JP)

(72) Inventor: Manase Mizutani, Nagoya (JP)

(73) Assignee: SINTOKOGIO, LTD., Nagoya (JP)

( * ) Notice: Subject to any disclaimer, the term of this patent is extended or adjusted under 35 U.S.C. 154(b) by 428 days.

(21) Appl. No.: 18/138,158

(22) Filed: Apr. 24, 2023

(65) Prior Publication Data

US 2023/0341372 A1 Oct. 26, 2023

(30) Foreign Application Priority Data

Apr. 26, 2022 (JP) ................................. 2022-072360

(51) Int. Cl.
*G01N 33/497* (2006.01)
*A01G 7/00* (2006.01)
*G01N 1/24* (2006.01)

(52) U.S. Cl.
CPC ............. *G01N 33/497* (2013.01); *A01G 7/00* (2013.01); *G01N 1/24* (2013.01); *G01N 33/4977* (2024.05)

(58) Field of Classification Search
CPC ............. G01N 33/497; G01N 33/4975; G01N 33/4977; G01N 33/0098
See application file for complete search history.

(56) References Cited

U.S. PATENT DOCUMENTS

2018/0259496 A1 * 9/2018 McPeek ............... G01N 33/025
2019/0124865 A1 5/2019 Sunnen 2020/0126198 A1 4/2020 Hirooka et al.
2021/0018479 A1 * 1/2021 Watanabe .............. G01N 27/02
2022/0276214 A1 9/2022 Yamamoto
2024/0003850 A1 1/2024 Oralkan et al.

FOREIGN PATENT DOCUMENTS

| CN | 106908488 A | 6/2017 |
|---|---|---|
| GB | 2197486 A | 5/1988 |
| JP | S63-159748 A | 7/1988 |
| JP | H2-304352 A | 12/1990 |
| JP | H8-242857 A | 9/1996 |
| JP | 2005-013056 A | 1/2005 |
| JP | 2011-002270 A | 1/2011 |
| JP | 2016-065868 A | 4/2016 |
| JP | 2020-064466 A | 4/2020 |
| JP | WO2019/082942 A1 | 9/2020 |
| JP | 6825157 B1 | 2/2021 |
| JP | 2021-069363 A | 5/2021 |
| JP | 2021-087382 A | 6/2021 |
| WO | WO-2019/082942 A1 | 5/2019 |
| WO | WO-2019/237200 A1 | 12/2019 |

OTHER PUBLICATIONS

Extended European Search Report issued Sep. 26, 2023 in Application No. 23169446.4.
Japanese Office Action issued Nov. 25, 2025 in Application No. 2022-072360.

* cited by examiner

*Primary Examiner* — Herbert K Roberts
(74) *Attorney, Agent, or Firm* — Faegre Drinker Biddle & Reath LLP

(57) ABSTRACT

The plant state detection system includes an odor detector including an odor detection unit configured to detect an odorant emitted from a plant, and a plant state detector configured to acquire odor information detected by the odor detection unit and detect a state of the plant based on the odor information.

6 Claims, 6 Drawing Sheets

Figure 1:
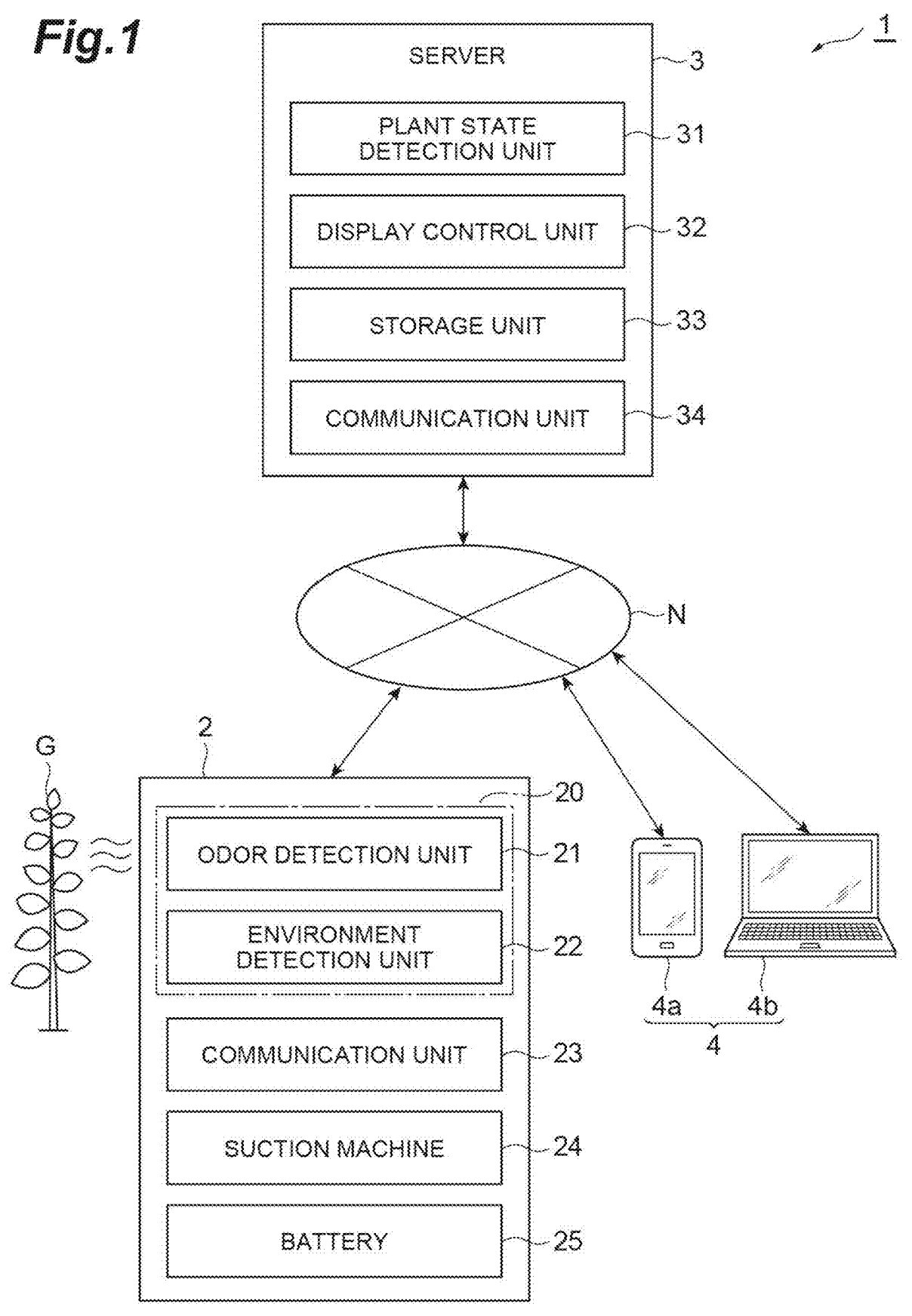

SERVER — 3

| PLANT STATE DETECTION UNIT | — 31 |

| DISPLAY CONTROL UNIT | — 32 |

| STORAGE UNIT | — 33 |

| COMMUNICATION UNIT | — 34 |

N

G

2

20

| ODOR DETECTION UNIT | — 21 |

| ENVIRONMENT DETECTION UNIT | — 22 |

| COMMUNICATION UNIT | — 23 |

| SUCTION MACHINE | — 24 |

| BATTERY | — 25 |

4a    4b

4

PLANT STATE DETECTION SYSTEM AND ODOR DETECTOR

CROSS-REFERENCE TO RELATED APPLICATION

This application is based on Japanese Patent Application No. 2022-072360 filed with Japan Patent Office on Apr. 26, 2022, the entire contents of which are hereby incorporated by reference.

TECHNICAL FIELD

The present invention relates to a plant state detection system and an odor detector.

BACKGROUND

Japanese Patent Application Publication No. 2020-64466 discloses, as an apparatus for detecting a plant state, an apparatus that captures an image of a crop and analyzes the captured image to grasp a growth state of the crop or a damage state caused by pests.

SUMMARY

However, it is difficult for the device described in Japanese Patent Application Publication No. 2020-64466 to accurately detect the plant state. The device described in Japanese Patent Application Publication No. 2020-64466, which captures an image of a plant and detects a plant state, can only detect the state of the plant in a range in which the image is captured, and may fail to detect the state of the plant when a disease, food damage, or the like occurs in a range in which the image is not captured.

The present disclosure provides a plant state detection system and an odor detector capable of accurately detecting a plant state.

That is, a plant state detection system according to one aspect of the present disclosure includes an odor detector including an odor detection unit configured to detect an odorant emitted from a plant, and a plant state detector configured to acquire odor information detected by the odor detection unit and detect a state of the plant based on the odor information. According to this plant state detection system, it is possible to detect an odor emitted from a plant and detect the state of the plant based on the odor information. Therefore, the plant state detection system can accurately detect the state of the plant.

In the plant state detection system according to the aspect of the present disclosure, the odor detector may include an environment detection unit that detects at least one environment value among environment values of temperature, humidity, carbon dioxide concentration, and illuminance around the plant, and the plant state detector may detect or predict the state of the plant based on the environment value. In this case, the plant state detection system can detect at least one environment value of environment values of temperature, humidity, carbon dioxide concentration, and illuminance around the plant, and detect or predict the state of the plant based on the environment value.

In the plant state detection system according to one aspect of the present disclosure, the odor detector may further include a container configured to accommodate the odor detection unit, and a suction machine configured to suck air around the plant into the container. In this case, the odor detection unit is accommodated in the container, and the substance emitted from the plant can be drawn into the container by sucking air around the plant into the container. Therefore, diffusion of the odorant is suppressed, and the plant state detection system can increase the detection accuracy in the odor detector.

In the plant state detection system according to one aspect of the present disclosure, the odor detector may detect at least any one of green leaf volatiles, terpenes, a sulfur-based substance, and/or a moldy odor substance as the odorant. In this case, the plant state detection system can detect a feeding damage state of the plant by detecting the green scent substance as the odorant, detect an environmental stress state of the plant by detecting the terpene substance as the odorant, detect a putrefaction state of the plant by detecting the sulfur-based substance as the odorant, and detect a mold generation state of the plant by detecting the moldy odor substance as the odorant.

The plant state detection system according to one aspect of the present disclosure, may further include a plurality of odor detectors including the odor detector, and the plurality of odor detectors is arranged at equal intervals in a cultivation area in which plants are cultivated. In this case, the plant state detection system can accurately recognize the state of the plant at each location in the cultivation area by arranging the plurality of odor detectors at equal intervals in the cultivation area.

addition, the plant state detection system according to one aspect of the present disclosure may include a display control unit configured to display the state of the plant corresponding to an arrangement position of the plurality of odor detectors. In this case, by displaying the state of the plant corresponding to the arrangement position of the plurality of odor detectors, the plant state detection system allows a user to easily grasp the state of the plant in the cultivation area through the visual sense.

An odor detector according to an aspect of the present disclosure includes an odor detection unit configured to detect an odorant emitted from a plant, and an output unit configured to output odor information of the odorant detected by the odor detection unit as information for detecting a state of the plant. According to this odor detector, the odorant emitted from the plant is detected, and the odor information is output as information for detecting the state of the plant. As a result, the odor detector can detect the state of the plant based on the odor information of the plant, and can accurately detect the state of the plant.

The odor detector according to one aspect of the present disclosure may further include an environment detection unit configured to detect at least one environment value among environment values of temperature, humidity, carbon dioxide concentration, and illuminance around the plant, and the output unit may output the environment value detected by the environment detection unit as information for detecting the state of the plant. In this case, the odor detector may output the environment value of the plant in addition to the odor information as information for detecting the state of the plant. Therefore, the odor detector can detect and predict the state of the plant based on the information of the odor and the environment value.

In addition, the odor detector according to one aspect of the present disclosure may include a container configured to accommodate the odor detection unit, and a suction machine configured to suck air around the plant into the container. In this case, the odor detection unit is accommodated in the container, and the odorant emitted from the plant can be drawn into the container by sucking air around the plant into the container. Therefore, diffusion of the odorant is suppressed, and the odor detector can increase the detection accuracy of the odorant.

In the odor detector according to the aspect of the present disclosure, the odor detection unit may detect at least one of green leaf volatiles, terpenes, a sulfur-based substance, and/or a moldy odor substance as the odorant. In this case, the odor detector can detect a feeding damage state of the plant by detecting the green scent substance as the odorant, and can detect an environmental stress state of the plant by detecting the terpene substance as the odorant. In addition, the odor detector may detect a putrefaction state of the plant by detecting a sulfur-based substance as the odorant, and may detect a mold generation state of the plant by detecting a moldy odor substance as the odorant.

In addition, in the odor detector according to one aspect of the present disclosure may include a plurality of odor detection units including the odor detection unit, and the plurality of odor detection units may be arranged at equal intervals in a cultivation area in which plants are cultivated. In this case, by arranging the plurality of odor detection units at equal intervals in the cultivation area, it is possible to accurately recognize the state of the plant at each location in the cultivation area.

According to the present disclosure, it is possible to accurately detect a plant state.

BRIEF DESCRIPTION OF THE DRAWINGS

FIG. 1 is a diagram showing an outline of an electrical configuration of a plant state detection system and an odor detector according to an embodiment of the present disclosure.

DETAILED DESCRIPTION

Figure 2:
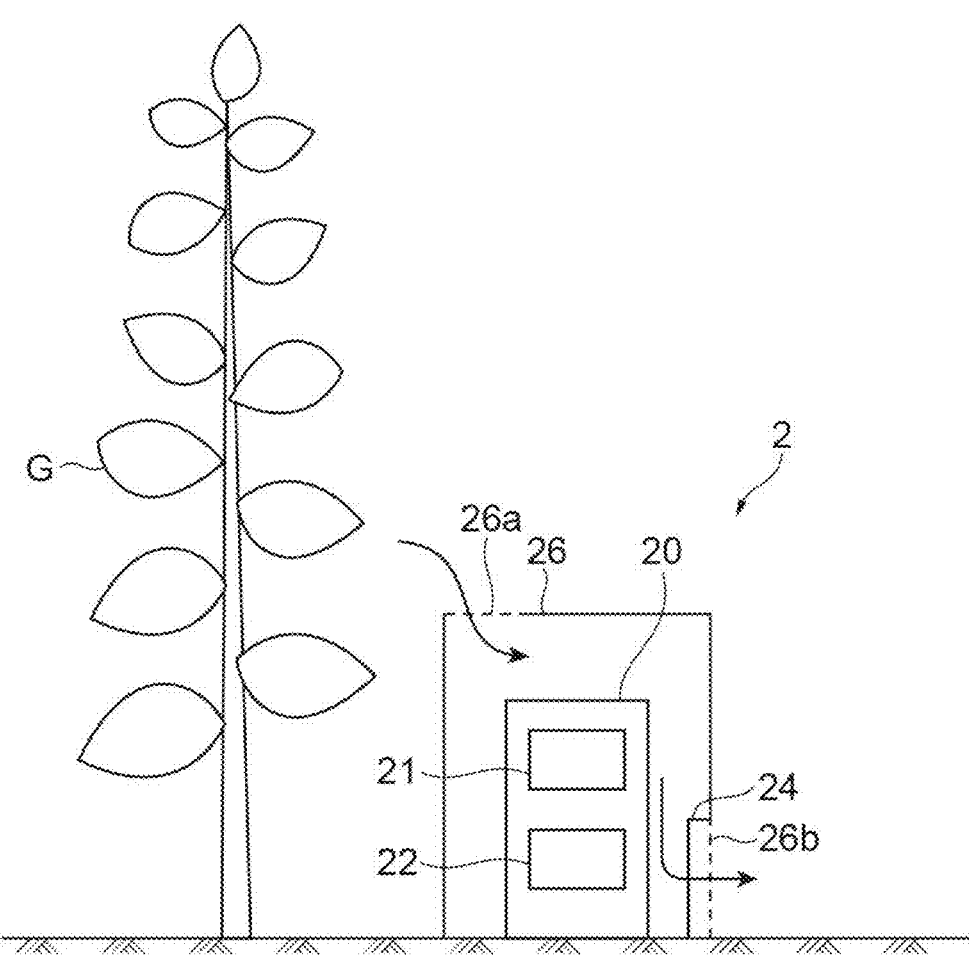
FIG. 2 is a diagram showing an outline of a configuration and an installation mode of the odor detector of FIG. 1.

Hereinafter, embodiments of the present disclosure will be described with reference to the drawings. In the following description, the same or corresponding elements are denoted by the same reference numerals, and redundant description is omitted.

Figure 3:
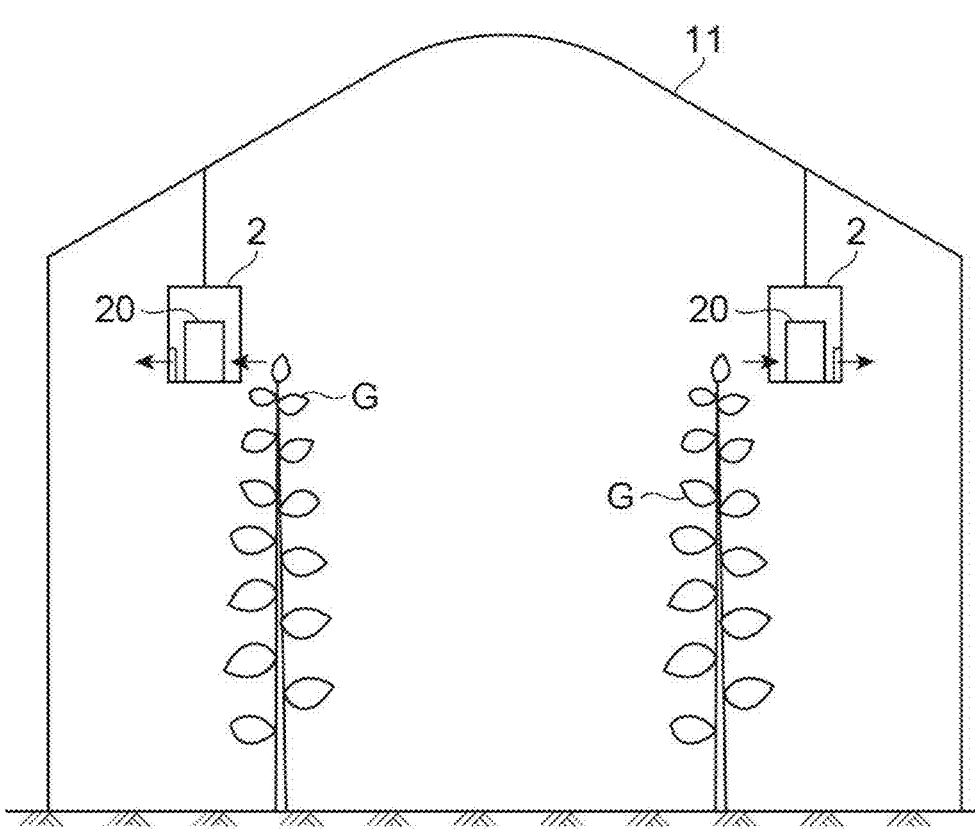
FIG. 3 is a diagram showing an example of an installation mode of the odor detector shown in FIG. 1.

FIG. 1 is a diagram showing an outline of an electrical configuration of a plant state detection system and an odor detector according to an embodiment of the present disclosure. FIGS. 2 and 3 are explanatory views of a configuration mode and an installation mode of the odor detector.

As shown in FIG. 1, a plant state detection system 1 is a system for detecting the state of a plant G by detecting odorant emitted from the plant G. The state of the plant G includes, for example, a health state or a growth state of the plant G. The plant state detection system 1 includes an odor detector 2 and a server 3 (an example of a plant state detector).

The odor detector 2 is a device that detects odorant emitted from the plant G, and is disposed in the vicinity of the plant G, for example. The plant G is a plant whose state is to be detected, and is, for example, a cultivated plant. The odor detector 2 is configured to transmit data information such as odor information to the server 3. For example, the odor detector 2 and the server 3 are configured to communicate via internet N. The odor detector 2 includes an odor detection unit 21, an environment detection unit 22, a communication unit 23 (an example of an output unit), a suction machine 24, and a battery 25.

The odor detection unit 21 and the environment detection unit 22 are provided as part of a sensor unit 20, for example, arranged in the same housing. The odor detection unit 21 is an odor sensor that detects odorant emitted from the plant G. The odorants emitted from the plant G includes odorants emitted directly from the plant G, as well as odorants emitted from those attached to the plant G and those attached to the vicinity of the plant G.

The odorants include, for example, green leaf volatiles (GLVs), terpenes, sulfur-based substances, and moldy odor substances. Green leaf volatiles are volatile substances such as aldehydes, alcohols, and esters thereof having a skeleton of six carbon atoms, and specific examples thereof include hexenol (leaf alcohol), cexenal (leaf aldehyde), and the like. Examples of the terpenes include organic compounds having an unsaturated hydrocarbon of $(C_5H_8)_n$ as a basic skeleton and terpene alcohols, and specific examples thereof include $\alpha$-pinene and $\beta$-caryophyllene. The sulfur-based substance is a sulfide compound such as hydrogen sulfide that emits a putrid odor of plants, and is, for example, dimethyl sulfide. Examples of the moldy odor substance include mold, trichloroanisole, geosmin, and methylisoborneol. Since the odor detection unit 21 detects the green scent substance as odorant, the odor detector 2 enables the server 3 to detect the feeding damage state of the plant G. In addition, since the odor detection unit 21 detects terpenes as odorants, the odor detector 2 enables the server 3 to detect the environmental stress state of the plant G. In addition, since the odor detection unit 21 detects the sulfur-based substance as odorant, the odor detector 2 enables the server 3 to detect the putrefaction state of the plant G. Further, the odor detection unit 21 detects the moldy odor substance as odorant, so that the odor detector 2 can cause the server 3 to detect the mold occurrence in the plant G.

The odor detection unit 21 detects at least one of green leaf volatiles, terpenes, sulfur-based substances, and/or moldy odor substances. The odor detection unit 21 may also sense some or all of these substances. Further, the odor detection unit 21 may detect odorants other than green leaf volatiles, terpenes, sulfur-based substances, and moldy odor substances, which can detect a plant state.

As the odor detection unit 21, for example, a sensor in which an organic film reacting with an odorant is applied to a metal semiconductor may be used. For example, a sensor including polyaniline as an organic film and tin oxide ($SnO_2$) as a metal semiconductor may be used. In the case of detecting a plurality of different odorants, a plurality of sensors may be used as the odor detection unit 21. In addition, a sensor other than the above-described sensors may be used as the odor detection unit 21 as long as the sensor can detect an odorant.

The environment detection unit 22 is a sensor for sensing the growth environment of the plant G. The environment detection unit 22 detects at least one environment value among environment values of temperature, humidity, carbon dioxide concentration and illumination around the plant G. The environment detection unit 22 may detect a part or all of environment values of temperature, humidity, carbon dioxide concentration, and illumination around the plant G. As the environment detection unit 22, for example, a thermometer, a hygrometer, a carbon dioxide concentration meter, or an illuminometer is used. Further, the environment detection unit 22 may detect environment values other than the temperature, humidity, carbon dioxide concentration, and illumination around the plant G.

The sensor unit 20 may include an airflow sensor. The airflow sensor is a sensor that detects the flow of air around the sensor unit 20. The odor detector 2 can detect whether or not the air around the plant G is drawn to the sensor unit 20 side by detecting the flow of the air around the sensor unit 20 by the air flow sensor. In some cases, the environment detection unit 22 may be omitted from the sensor unit 20.

The communication unit 23 functions as an output unit that outputs odor information detected by the odor detection unit 21 as information for detecting the state of the plant G. For example, the communication unit 23 outputs odor information detected by the odor detection unit 21 to an external device. In this case, the communication unit 23 repeatedly outputs the odor information to the external device in a predetermined cycle. This allows the odor detector 2 to provide the plant G condition in real time. The odor information is, for example, the detection level of the odorant. When the odor detection unit 21 has a plurality of sensors, a plurality of odor information corresponding to the respective sensors are output. In addition to the odor information, the communication unit 23 may output environmental value information of the environment value detected by the environment detection unit 22 as information for detecting the state of the plant G. This the communication unit 23 is, for example, a communication device for communicating with the server 3, and is configured to be able to communicate with the server 3 via the internet N. The communication unit 23 may be, for example, a router for connecting the sensor unit 20 to the internet N or a wireless local area network (LAN) router that relays the connection to the router.

The suction machine 24 is a device for drawing air around the plant G to the sensor unit 20. As the suction machine 24, for example, a device capable of sucking air such as a pump or a fan is used. The battery 25 is a capacitor for supplying power to a device that needs power supply in the odor detector 2. Since the odor detector 2 is provided with the battery 25, it is not necessary to connect a power supply cable to the odor detector 2 to draw external power, and installation and handling of the odor detector 2 are facilitated. In some examples, the installation of the battery 25 is omitted in the odor detector 2, and operation is performed by an external power source.

As shown in FIG. 2, the odor detector 2 is placed at the plant G location. For example, the odor detector 2 is placed on soil where the plant G is planted. In this case, the odor detector 2 may be installed on the ground via a member such as a spacer. In addition, as shown in FIG. 3, when the odor detector 2 is placed in a facility 11 such as a plastic greenhouse, the odor detector 2 may be suspended from the top. FIG. 3 is a diagram showing an example of an installation mode of the odor detector shown in FIG. 1.

Figure 4:
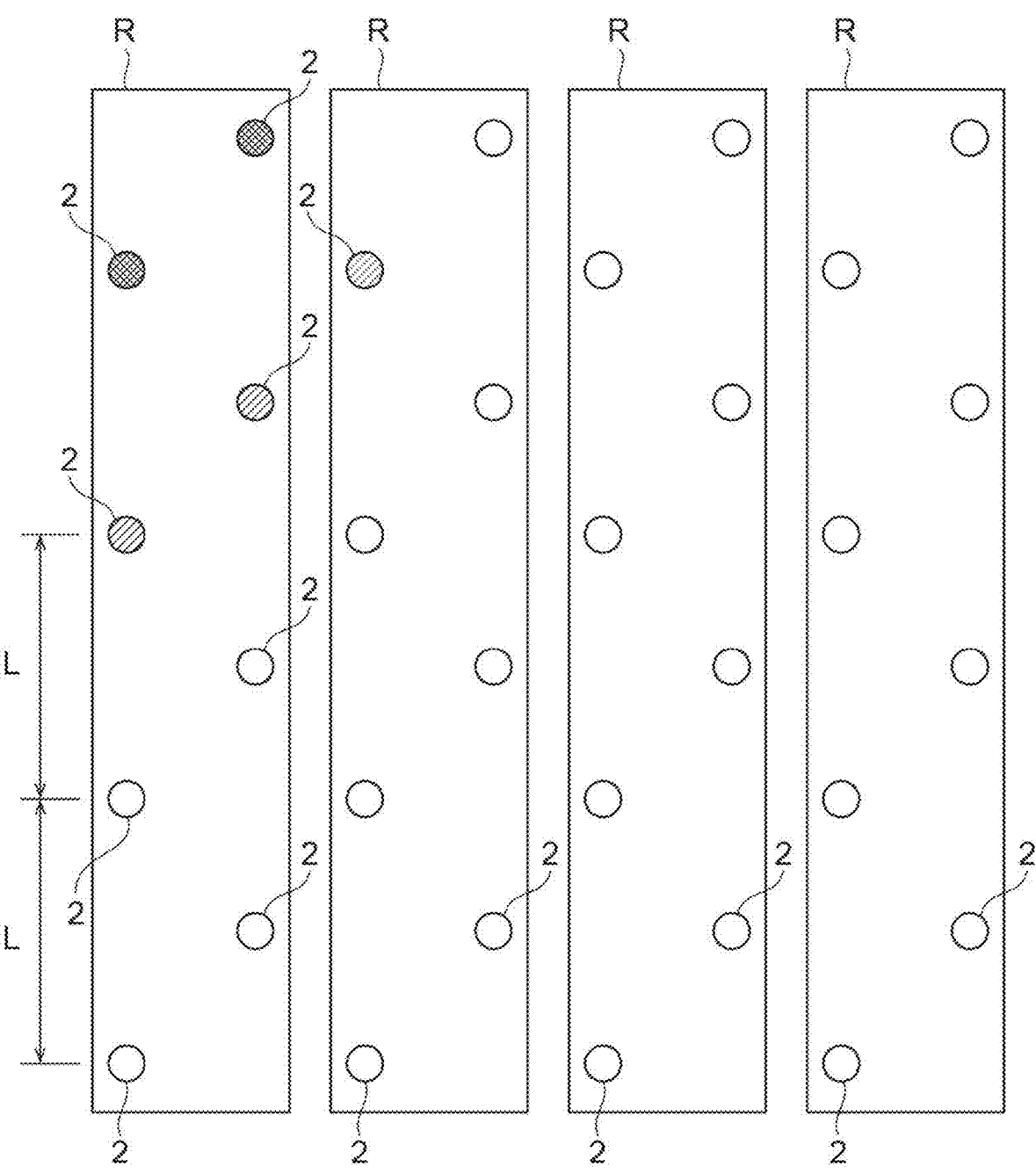
FIG. 4 is a diagram showing a display mode of a plant state in the plant state detection system of FIG. 1.

Further, as shown in FIG. 4, a plurality of the odor detectors 2 may be installed in a cultivation region R in which a plurality of the plant G is cultivated. FIG. 4 is a diagram showing an installation mode of the odor detectors 2 and a display mode of a plant state, in which the cultivation region R is viewed from above. In this case, the plurality of installed the odor detectors 2 is arranged at equal intervals. For example, the odor detectors 2 may be placed in the same an interval L for an adjacent the odor detectors 2 in the cultivation region R. By arranging the odor detectors 2 in this manner, the server 3 can accurately recognize the state of the plant G at each location in the cultivation region R. Although FIG. 4 shows a case where the plurality of odor detectors 2 is arranged at equal intervals in the vertical direction in the cultivation region R, the odor detectors 2 may be arranged at equal intervals in the horizontal direction or the oblique direction. Here, equal intervals include substantially equal intervals. The cultivation region R represents a cultivation lot of the plants G, and a plurality of the plants G are cultivated in the cultivation region R.

In FIG. 2, the odor detector 2 has a container 26. The container 26 is a member for accommodating the odor detection unit 21, and for example, a box-shaped member covering the odor detection unit 21 is used. The container 26 may be a rectangular parallelepiped as shown in FIG. 2, or may have a shape other than the rectangular parallelepiped as long as the shape surrounds the odor detection unit 21. The container 26 is, for example, one that can be handled by hand. In FIG. 2, the sensor unit 20 is contained in the container 26, and the odor detection unit 21 and the environment detection unit 22 are contained in the container 26, however the environment detection unit 22 may be placed outside the container 26. Although the communication unit 23 is not shown in FIG. 2, the communication unit 23 may be installed inside the container 26 or outside the container 26.

A suction port 26a and a discharge port 26b are formed in the container 26. The suction port 26a and the discharge port 26b are openings that pass through the container 26. The suction port 26a is an opening for sucking air around the plant G into the container 26. The suction port 26a is formed, for example, on top of the container 26. The discharge port 26b is an opening for discharging air in the container 26 to the outside of the container 26. The discharge port 26b is formed at a lower portion of the container 26, for example.

The container 26 is provided with the suction machine 24. The suction machine 24 sucks air around the plant G into the container 26. The suction machine 24 is provided, for example, at a position of the discharge port 26b, and draws air around the plant G from the suction port 26a into the container 26 by discharging air in the container 26 from the discharge port 26b by driving. The suction machine 24 may be provided at the position of the suction port 26a, and air may be sucked from the suction port 26a by driving the suction machine 24.

As described above, the container 26 for accommodating the odor detection unit 21 is provided, and the air around the plant G is sucked into the container 26 to detect the odorant, whereby the detection accuracy of the odorant can be enhanced in the odor detector 2. That is, by sucking air around the plant G into the container 26, the odor detector 2 can suppress diffusion of odorant in the plant G and maintain a high concentration of odorant. Thus, the odor detector 2 can improve the detection accuracy of the odorant of the plant G.

In FIG. 1, the server 3 is a plant state detector that acquires odor information detected by the odor detection unit 21 and detects the state of the plant G based on the odor information. In addition to the odor information, the server 3 may acquire environmental value information, detect the state of the plant G based on the odor information and the environmental value information, and predict the state of the plant G. The server 3 is configured by a computer including, for example, a central processing unit (CPU), a read only memory (ROM), and a random-access memory (RAM), records odor information and environmental value information transmitted from the odor detector 2, and detects and predicts the state of the plant G based on the information. This the server 3 functions as a main device of cloud computing in the plant state detection system 1, for example. That is, the server 3 provides plant state information indicating the state of the plant G to a terminal device 4. For example, the server 3 enables cloud services by providing plant state information to the terminal device 4 that has accessed the server 3.

The server 3 includes a plant state detection unit 31, a display control unit 32, a storage unit 33, and a communication unit 34. The plant state detection unit 31 detects and predicts the plant G conditions based on odor information and environmental value information. For example, the plant state detection unit 31 obtains the sensed level of odorant of the plant G as odor information. The detection level corresponds to the concentration of the odorant. The plant state detection unit 31 then determines the state of the plant G based on the sensed level of the odorant. For example, a table in which the detection level of the odorant and the state of the plant G are associated with each other and relationship information such as a determination threshold are set for the plant state detection unit 31. Using this relationship, the plant state detection unit 31 can determine the plant G condition from the sensed level of odorant.

In particular, when the odorant is green leaf volatiles, the plant state detection unit 31 may determine a feeding damage state of the plant G. That is, the plant state detection unit 31 determines whether the plant G is in the normal state, the caution state, or the warning state based on the detection level of the green scent substance. The normal state is a state in which the detection level is low and there is no feeding damage, the caution state is a state in which the detection level exceeds the caution level and there is a risk of feeding damage, and the warning state is a state in which the detection level exceeds the warning level and feeding damage has occurred. In this case, the plant state detection unit 31 determines the state of the plant G in three stages, however, may determine the state in two stages or four or more stages.

Also, when the odorant is terpene substance, the environmental stress state of the plant G can be determined by the plant state detection unit 31. That is, the plant state detection unit 31 determines whether the plant G is in the normal state, the caution state, or the warning state based on the detection level of the terpene substance. The normal state is a state in which the detection level is low and there is no problem with environmental stress, the caution state is a state in which the detection level exceeds the caution level and there is a possibility of environmental stress occurring, and the warning state is a state in which the detection level exceeds the warning level and environmental stress occurs. In this case, the plant state detection unit 31 determines the state of the plant G in three stages, however, may determine the state in two stages or four or more stages.

Also, when the odorant is a sulfur-based substance, the plant state detection unit 31 may determine the putrefaction state of the plant G. That is, the plant state detection unit 31 determines whether the plant G is in the normal state, the caution state, or the warning state based on the detection level of the sulfur-based substance. The normal state is a state where the detection level is low and there is no putrefaction, the caution state is a state where the detection level exceeds the caution level and there is a possibility that putrefaction has occurred, and the warning state is a state where the detection level exceeds the warning level and there is putrefaction. In this case, the plant state detection unit 31 determines the state of the plant G in three stages, however, may determine the state in two stages or four or more stages.

Also, when the odorant is a moldy odor substance, the plant state detection unit 31 may determine the mold generation state in the plant G. That is, the plant state detection unit 31 determines whether the plant G is in the normal state, the caution state, or the warning state based on the detection level of the moldy odor substance. The normal state is a state in which the detection level is low and no mold is generated, the caution state is a state in which the detection level exceeds the caution level and there is a possibility that mold is generated, and the warning state is a state in which the detection level exceeds the warning level and mold is generated. In this case, the plant state detection unit 31 determines the state of the plant G in three stages, however, may determine the state in two stages or four or more stages.

In addition, the plant state detection unit 31 acquires environment values of temperature, humidity, carbon dioxide concentration, and illumination around the plant G as an environmental value information. The plant state detection unit 31 then determines the state of the plant G based on the environment value. For example, in the plant state detection unit 31, a table in which the environment value and the state of the plant G are associated with each other, a determination threshold value, and the like are set. Using this relationship, the plant state detection unit 31 can determine the state of the plant G from the environment value. That is, the plant state detection unit 31 can predict the occurrence state of mold with respect to the plant G based on the ambient temperature, humidity, carbon dioxide concentration, and illumination of the plant G. In addition, the plant state detection unit 31 can more accurately detect and predict the occurrence state of the mold by performing determination by combining the odor information of the moldy odor substance and the environmental value information.

The display control unit 32 displays the state of the plant G based on the odor detection level in the odor detector 2. For example, the display control unit 32 generates display date in which the odor detector 2 and the state of the plant G are associated with each other based on the state of the plant G detected by the plant state detection unit 31. Then, the display control unit 32 displays the odor detector 2 and the state of the plant G in association with each other so as to be browsable in the terminal device 4 or the like.

To be specific, as shown in FIG. 4, when a plurality of the odor detection unit 21 are installed in the cultivation region R, the display control unit 32 displays the state of the plant G corresponding to the arrangement position in the odor detector 2. The display mode is changed according to the state of the plant G. For example, the better the state of the plant G, the lighter the display mode. In other words, the display mode is displayed in a darker manner as the state of the plant G is worse. The display control unit 32 can visually and easily grasp the state of the plant G in the cultivation region R by setting different display modes according to the state of the plant G. In addition, the plant G can be efficiently managed in the case of cultivating the plant G in a large-scale cultivation facility, cultivating the plant G in a wide the cultivation region R, cultivating the plant G in a plurality of the cultivation region R, or the like.

Note that the display mode of the plant G state may be a different color according to the plant G state. For example, when the state of the plant G is good, the color is made inconspicuous. For example, the color is green when the state of the plant G is good, yellow when the state of the plant G is not so good, and red when the state of the plant G is bad. In addition, the display control unit 32 may be displayed with a different mark according to the state of the plant G as the display mode, or the state of the plant G may be displayed with characters. In addition, the display control unit 32 may display the state of the plant G in a table format by assigning numbers to the odor detection unit 21 as the display mode.

The storage unit 33 records odor information and the plant G condition information. In this case, odor information repeatedly transmitted from the odor detector 2 in a predetermined cycle is recorded, and the state of the plant G based on the odor information is recorded.

The communication unit 34 has the ability to communicate with the odor detector 2. For example, the communication unit 34 can communicate with the odor detector 2 via the internet N and receive odor information transmitted from the odor detector 2. In addition, the communication unit 34 provides information on the state of the plant G detected based on the odor information to the terminal device 4. For example, by accessing the server 3 using the terminal device 4, it is possible to confirm or recognize the status of the plant G through the terminal device 4 even if not at the plant G location. The terminal device 4 is, for example, a smartphone 4a, a personal computer 4b, or the like. The terminal device 4 may also be another terminal device, such as a tablet.

Next, the use method and operation of the plant state detection system 1 and the odor detector 2 according to the present embodiment will be described.

Figure 5:
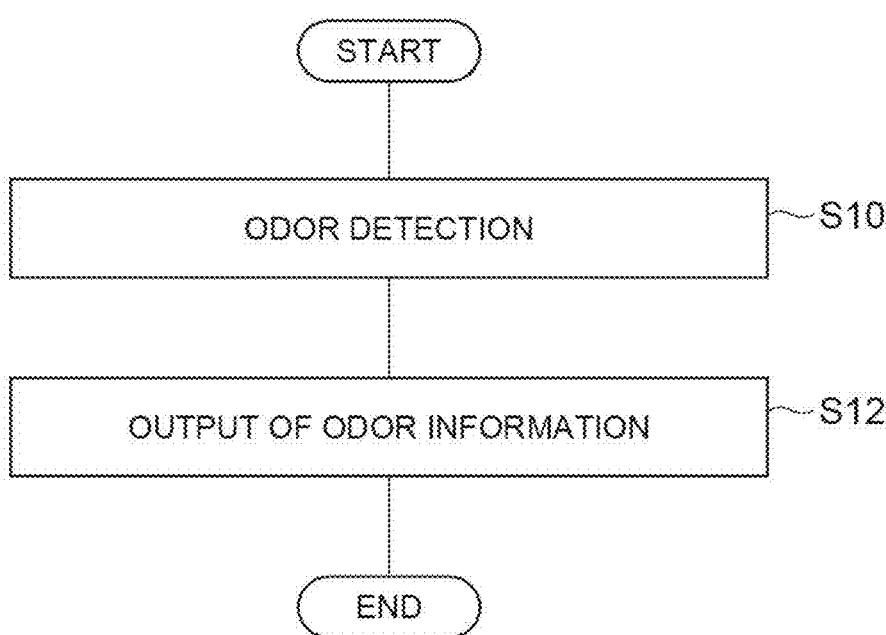
FIG. 5 is a flowchart showing control processing of the odor detector shown in FIG. 1.
Figure 6:
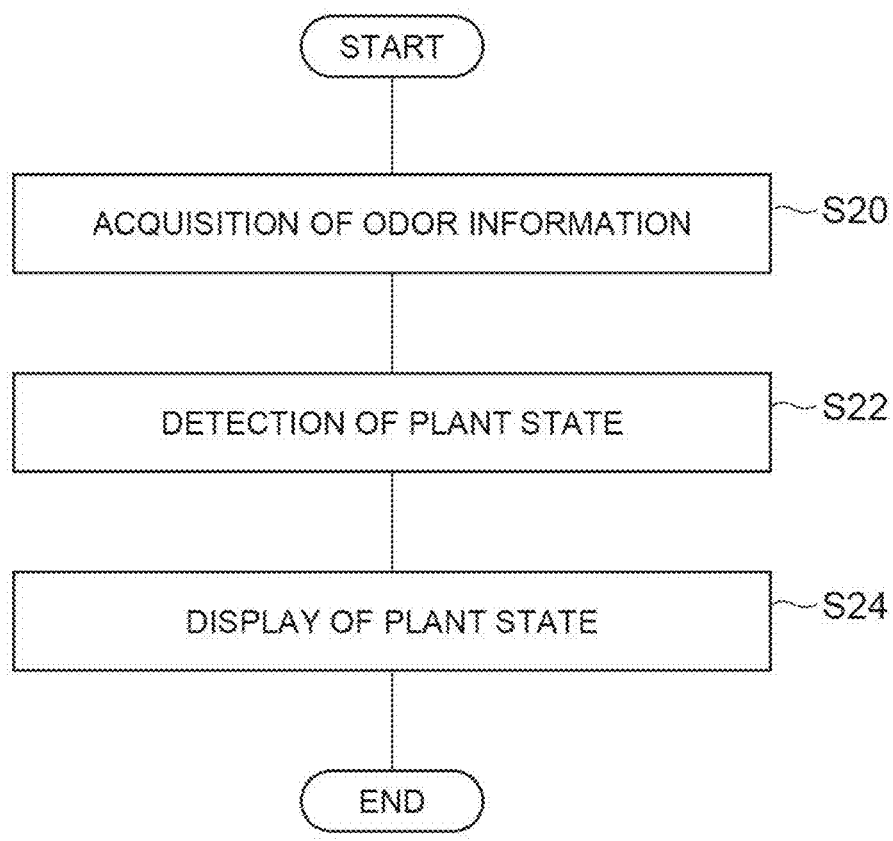
FIG. 6 is a flowchart showing a control process of the server of the plant state detection system of FIG. 1.

FIG. 5 is a flow chart showing the operation of the odor detector 2. FIG. 6 is a flow chart showing the operation of the server 3 in the plant state detection system 1.

First, as shown in FIGS. 2 and 3, the odor detector 2 is placed in a place where there is the plant G. The odor detector 2 is placed near the plant G. At this time, the odor detector 2 may be placed on the ground or may be lifted from above. Further, as shown in FIG. 4, a plurality of the odor detectors 2 may be installed in the cultivation region R of the plant G. In this case, the odor detection units 21 of the odor detectors 2 are arranged at equal intervals. Thus, the state of the plant G at each place in the cultivation region R can be accurately recognized. The position of the odor detector 2 is displayed and registered in the cultivation region R. For example, the position of the odor detector 2 in the cultivation region R is set and registered so as to match the position of the display range.

Then, as shown in FIG. 5, the odor detector 2 executes odor detection processing. The series of control processing shown in FIG. 5 is repeatedly executed at a predetermined cycle by the odor detector 2.

First, step S10 (hereinafter simply referred to as S10) in FIG. 5 is performed. The same applies to the subsequent steps), odor detection is performed. Odor detection is a process of detecting odorant emitted from the plant G. For example, the odor detection unit 21 senses odorant emitted from the plant G. The detection of the odorant is detected by the odor detection unit 21 as the concentration of the odorant or odor strength and is processed and recorded by the odor detector 2 as odor information. In a case where a plurality of sensors is provided in the odor detection unit 21 to perform detection of a plurality of kinds of odorants, respective odor information is recorded.

In addition to odor detection, environment value detection may be performed in the S10. The detection of the environment value is a process of detecting the growth environment of the plant G. For example, the environment detection unit 22 detects at least one environment value among environment values of temperature, humidity, carbon dioxide concentration, and illumination around the plant G. The sensed environment value is data processed and recorded by the odor detector 2 as environmental value information.

When odorant is detected in the S10, the suction machine 24 is activated. That is, as shown in FIG. 2, the suction machine 24 is activated and air around the plant G is sucked into the container 26. Thus, the odorant can be detected with high accuracy. That is, by accommodating the odor detection unit 21 in the container 26 and sucking the air around the plant G into the container 26, it is possible to suppress the odorant from diffusing around the plant G. Therefore, odor detection can be performed without lowering the concentration of odorant, and the detection accuracy is improved. In addition, by sucking the air around the plant G into the container 26, it is possible to reliably attract and detect the odorant even when the air flows in the odor detector 2 and reverse direction around the plant G.

Then, the processing shifts to S12 of FIG. 5, and odor information is output. The output of odor information is a process of transmitting the odor information of the odorant detected in the odor detection unit 21 to the server 3. For example, the communication unit 23 transmits odor information of the odorant sensed by the odor detection unit 21 to the server 3 via the internet N. At this time, when the environment value of the plant G is detected, environmental value information is transmitted to the server 3 together with the odor information. When the S12 processing is completed, the series of control processing in FIG. 5 is completed.

On the other hand, in the server 3, plant state detection processing is executed as shown in FIG. 6. This plant state detection processing is repeatedly executed at a predetermined cycle by the server 3.

First, as shown in S20 of FIG. 6, odor information is acquired. The acquisition of the odor information is processing for acquiring the odor information transmitted from the odor detector 2. For example, the communication unit 34 receives odor information transmitted from the odor detector 2. Then, the received odor information is recorded in the storage unit 33. When environmental value information is received together with the odor information, the environmental value information is also recorded in the storage unit 33.

Then, the processing shifts to S22, and the plant state is detected. The detection of the plant state is a process of detecting the state of the plant G based on the odor information. When environmental value information is acquired in addition to the odor information, the state of the plant G may be detected based on the odor information and the environmental value information. For example, the plant state detection unit 31 detects the status of the plant G based on the plant G odor information. That is, the plant state detection unit 31 detects the state of the plant G based on the sensed level of the odorant.

In particular, the plant state detection unit 31 may detect the feeding damage state of the plant G when the sensed odorant is green leaf volatiles. Then, the plant state detection unit 31 can detect that the feeding damage degree of the plant G is larger as the detection level of odorant is higher. In addition, the plant state detection unit 31 may detect an environmental stress state of the plant G when the sensed odorant is terpenes. Then, the plant state detection unit 31 can detect that the environmental stress of the plant G is larger as the detection level of the odorant is higher. In addition, the plant state detection unit 31 may detect a putrefaction state of the plant G when the sensed odorant is a sulfur-based substance. Then, the plant state detection unit 31 can detect that the putrefaction degree of the plant G is larger as the detection level of the odorant is higher.

In addition, when the detected odorant is a moldy odor substance, the plant state detection unit 31 may detect a mold generation state of the plant G. Then, the plant state detection unit 31 can detect that the mold is more widely or densely generated around the plant G or the plant G as the detection level of odorant is higher. In this case, the plant state detection unit 31 can detect or predict the state of the plant G based on the environmental value information. That is, the plant state detection unit 31 can detect and predict the occurrence of mold by using some or all of the environment values of the temperature, humidity, carbon dioxide concentration, and illumination around the plant G in the environmental value information. For example, when the temperature is high, the humidity is high, and the illumination is low, it is possible to detect or predict that the plant state detection unit 31 is likely to have mold. Therefore, the plant state detection unit 31 can improve the detection accuracy and prediction accuracy by detecting and predicting the state of the plant G by combining the odor information and the environmental value information.

Then, the processing shifts to S24, and the plant state is displayed. In the display of the plant state, display date in which the states of the odor detector 2 and the plant G are associated with each other is generated based on the state of the plant G detected by the S22, and the state of the plant G is displayed in association with the odor detector 2. For example, as shown in FIG. 4, when a plurality of the odor detectors 2 is arranged in the cultivation region R, the state of the plant G is displayed corresponding to the arrangement position of the odor detector 2. FIG. 4 schematically shows the cultivation region R, and shows the quality of the state of the plant G in different shades corresponding to the odor detector 2. That is, the better the state of the plant G is, the lighter the display is, and the worse the state of the plant G is, the darker the display is. In FIG. 4, it can be seen that the plant G state of the upper left portion of the four the cultivation region R is bad. By setting a different display mode according to the state of the plant G, the plant state detection system 1 can easily grasp the state of the plant G in the cultivation region R through visual observation. In addition, the plant state detection system 1 can efficiently manage the plant G when cultivating the plant G in a large-scale cultivation facility, when cultivating the plant G in a wide the cultivation region R, or when cultivating the plant G in a plurality of the cultivation region R.

Note that the display mode of the plant G state may be a different color according to the plant G state. For example, when the state of the plant G is good, the color is made inconspicuous. For example, the color is green when the state of the plant G is good, yellow when the state of the plant G is not so good, and red when the state of the plant G is bad.

The state of the plant G shown in FIG. 4 is displayed in the terminal device 4 by accessing the server 3 with the terminal device 4. Accordingly, the user can check the state of the plant G using the terminal device 4. Therefore, even a user at a place remote from the plant G can confirm the state of the plant G in real time. When the S24 processing is completed, the series of control processing in FIG. 6 is completed.

As described above, according to the plant state detection system 1 and the odor detector 2 of the present embodiment, the odor emitted from the plant G is detected, and the odor information is output as information for detecting the state of the plant G. Accordingly, the plant state detection system 1 and the odor detector 2 can detect the state of the plant G based on the odor information of the plant G, and can detect the state of the plant G with high accuracy. For example, when an image of the plant G is captured and the state of a plant is detected based on the captured image, it is difficult to detect the state of a portion of the plant G that is not captured. On the other hand, in the plant state detection system 1 and the odor detector 2 according to the present embodiment, since the state of the plant G is detected based on the odor information of the plant G, it is possible to detect the state of the plant G in a portion distant from the odor detection unit 21 or a portion in the shadow. Therefore, the plant state detection system 1 and the odor detector 2 according to the present embodiment can accurately detect the state of the plant G.

In addition, according to the plant state detection system 1 and the odor detector 2 of the present embodiment, the state of the plant G can be detected based on the environment value of the plant G in addition to the odor information of the plant G. Therefore, the plant state detection system 1 and the odor detector 2 according to the present embodiment can more accurately detect and predict the state of the plant based on the odor information and the environmental value information.

Further, according to the plant state detection system 1 and the odor detector 2 of the present embodiment, the odor detection unit 21 can be housed in the container 26, air around the plant G can be sucked into the container 26, and odorant emitted from the plant G can be drawn into the container 26. For this reason, in the plant state detection system 1 and the odor detector 2 according to the present embodiment, the odorant is suppressed from being diffused, and the detection accuracy of the odorant can be improved.

According to the plant state detection system 1 and the odor detector 2 of the present embodiment, at least one of green leaf volatiles, terpenes, sulfur-based substances, and/or moldy odor substances is detected as an odorant by the odor detection unit 21. Therefore, the plant state detection system 1 and the odor detector 2 according to the present embodiment can detect the feeding damage state of the plant G by detecting green leaf volatiles as odorants, can detect the environmental stress state of the plant G by detecting terpenes as odorants, can detect the putrefaction state of the plant G by detecting sulfur-based substances as odorants, and can detect the mold generation state of plants by detecting moldy odor substances as odorants.

Further, according to the plant state detection system 1 and the odor detector 2 of the present embodiment, a plurality of the odor detection unit 21 are provided in the cultivation region R in which a plurality of the plant G is cultivated, and are installed at equal intervals. Therefore, the plant state detection system 1 and the odor detector 2 according to the present embodiment can accurately recognize the state of the plant G at each place in the cultivation region R.

In addition, the plant state detection system 1 according to the present embodiment includes the display control unit 32 that displays the state of the plant G corresponding to the arrangement positions of a plurality of the odor detector 2. Therefore, the plant state detection system 1 can display the state of the plant G corresponding to the arrangement positions of the plurality of the odor detector 2, and can easily grasp the state of the plant G in the cultivation region R through visual observation.

Although the embodiments of the present disclosure have been described, these embodiments describe some of the embodiments of the plant state detection system and the odor detector according to the present disclosure, and the plant state detection system and the odor detector according to the present disclosure are not limited to those described in the above embodiments. The plant state detection system and the odor detector according to the present disclosure may be obtained by modifying the plant state detection system and the odor detector according to the above-described embodiment or applying the modified plant state detection system and the odor detector to another plant state detection system or described in each claim.

For example, in the plant state detection system 1 and the odor detector 2 according to the above-described embodiment, odor information detected in the odor detector 2 is transmitted to the server 3 via the internet N. However, odor information may be transmitted via a communication line other than the internet N. In addition, the odor detector 2 may be connected to the plant state detector wire or wirelessly, and the odor information detected by the odor detector 2 may be transmitted to the plant state detector. In this case, by causing the personal computer to function as a plant state detector, the plant state can be detected by the personal computer and the state of the plant G can be displayed.

Further, in the plant state detection system 1 and the odor detector 2 according to the above-described embodiment, the container 26 accommodating the odor detection unit 21 is installed in the vicinity of the plant G. However, the plant G may be accommodated inside the container 26 to detect the odorant of the plant G and detect the state of the plant G.

In addition, the plurality of the odor detector 2 may be freely installed at irregular intervals. For example, each of the plurality of the odor detector 2 may be installed at a position where odorant emitted from the plant G is easily detected. In this case, the server 3 may be configured to be able to acquire the installation positions of the plurality of the odor detector 2. The display control unit 32 of the server 3 can display the state of the odor detector 2 and the plant G in association with each other based on the installation position.

What is claimed is:

1. A plant state detection system comprising:

a plurality of odor detectors arranged in a cultivation area in which plants are cultivated, each odor detector including an odor detection unit configured to detect an odorant emitted from a plant; and a plant state detector configured to acquire odor information detected by the odor detection unit and detect states of the plants based on the odor information, wherein the plant state detector includes a display control unit configured to display the states of the plants corresponding to arrangement positions of the plurality of odor detectors, and to cause display modes for the respective arrangement positions in the cultivation area to be changed stepwise according to the degree of plant state, wherein the plant state detector is configured to determine whether the plant is in a normal state, a caution state, or a warning state based on a detection level of the odorant; and wherein the display control unit is configured to display the normal state, the caution state, and the warning state in different colors, and to cause display modes respectively corresponding to the normal state, the caution state, and the warning state to be displayed such that the display becomes darker as the state of the plant becomes worse.

2. The plant state detection system according to claim 1, wherein each odor detector comprises an environment detection unit configured to detect at least one environment value among environment values of temperature, humidity, carbon dioxide concentration, and illuminance around the plant, and wherein the plant state detector is configured to detect or predict the states of the plants based on the at least one environment value.

3. The plant state detection system according to claim 1, wherein each odor detector further comprises a container configured to accommodate the odor detection unit, and a suction machine configured to suck air around the plant into the container.

4. The plant state detection system according to claim 1, wherein each odor detector is configured to detect at least one of green leaf volatiles, terpenes, a sulfur-based substance, and/or a moldy odor substance as the odorant.

5. The plant state detection system according to claim 1, wherein the plurality of odor detectors are arranged at equal intervals in the cultivation area.

6. The plant state detection system according to claim 1, wherein the display control unit is configured to cause temporal changes in the state of plants in the cultivation area to be displayed.

* * * * *